United States Patent
Chin et al.

(10) Patent No.: US 9,717,538 B2
(45) Date of Patent: Aug. 1, 2017

(54) SYSTEM AND METHOD FOR BONE FUSING IMPLANTS AND IMPLANT INSERTION TOOLS

(71) Applicants: Kingsley R. Chin, Wilton Manors, FL (US); Richard Francis, Houston, TX (US); Craig Henshaw, Charlestown, MA (US); Jeremy Crossgrove, Storrs, CT (US); August Kawski, Gloucester, MA (US)

(72) Inventors: Kingsley R. Chin, Wilton Manors, FL (US); Richard Francis, Houston, TX (US); Craig Henshaw, Charlestown, MA (US); Jeremy Crossgrove, Storrs, CT (US); August Kawski, Gloucester, MA (US)

(73) Assignee: SPINEFRONTIER, INC, Malden, MA (US)

( * ) Notice: Subject to any disclaimer, the term of this patent is extended or adjusted under 35 U.S.C. 154(b) by 498 days.

(21) Appl. No.: 14/485,903

(22) Filed: Sep. 15, 2014

(65) Prior Publication Data
US 2015/0080972 A1     Mar. 19, 2015

Related U.S. Application Data

(60) Provisional application No. 61/878,141, filed on Sep. 16, 2013.

(51) Int. Cl.
*A61B 17/70*     (2006.01)
*A61B 17/16*     (2006.01)
(Continued)

(52) U.S. Cl.
CPC ...... *A61B 17/7055* (2013.01); *A61B 17/1655* (2013.01); *A61B 17/1659* (2013.01);
(Continued)

(58) Field of Classification Search
CPC .................................................. A61B 17/7055
See application file for complete search history.

(56) References Cited

U.S. PATENT DOCUMENTS 5,334,205 A * 8/1994 Cain .................. A61B 17/1742
606/86 R
6,159,179 A 12/2000 Simonson
(Continued)

*Primary Examiner* — Andrew Yang
(74) *Attorney, Agent, or Firm* — AKC Patents, LLC; Aliki K. Collins

(57) ABSTRACT

A method for fusing two adjacent stacked bones includes the following. First, inserting first and second pins into first and second locations of a first surface of one of the two adjacent stacked bones, respectively. Next, inserting a dilator over each of the first and second pins to dilate tissue around the first and second pins. Next, inserting a tissue protector over the dilator and removing the dilator. Next, inserting a cannulated drill through the tissue protector over each of the first and second pins and drilling first and second openings in the first and second locations, respectively, wherein the first and second opening extend through the two adjacent stacked bones. Next, tapping threads in the first opening and inserting a first bone fusing implant in the first opening, wherein the first bone fusing implant comprises threads configured to engage the threads of the first opening. Next, impacting a broach into the second opening to generate a pattern corresponding to a pattern of a second bone fusing implant and then inserting the second bone fusing implant in the second opening.

24 Claims, 21 Drawing Sheets

(51) Int. Cl.

| | | |
|---|---|---|
| *A61B 17/84* | (2006.01) | |
| *A61B 17/86* | (2006.01) | |
| *A61B 17/17* | (2006.01) | |
| A61B 17/02 | (2006.01) | |
| A61B 17/92 | (2006.01) | |
| A61F 2/30 | (2006.01) | |
| A61B 17/00 | (2006.01) | |
| A61B 17/32 | (2006.01) | |
| A61B 90/00 | (2016.01) | |

(52) U.S. Cl.
CPC ........ *A61B 17/1739* (2013.01); *A61B 17/846* (2013.01); *A61B 17/863* (2013.01); *A61B 17/864* (2013.01); *A61B 17/8645* (2013.01); A61B 17/0218 (2013.01); A61B 17/866 (2013.01); A61B 2017/0042 (2013.01); A61B 2017/320056 (2013.01); A61B 2017/922 (2013.01); A61B 2090/061 (2016.02); A61B 2090/0807 (2016.02); A61F 2002/30995 (2013.01)

(56) References Cited

U.S. PATENT DOCUMENTS

| | | | |
|---|---|---|---|
| 7,494,489 B2 | 2/2009 | Roh | |
| 7,901,438 B2 | 3/2011 | Culbert et al. | |
| 8,388,667 B2 * | 3/2013 | Reiley | A61B 17/1659 606/300 |
| 9,241,798 B2 * | 1/2016 | Petersen | A61F 2/30988 |
| 2008/0147079 A1 | 6/2008 | Chin et al. | |
| 2010/0004657 A1 | 1/2010 | Dudasik | |
| 2010/0268232 A1 | 10/2010 | Betz et al. | |

* cited by examiner

SYSTEM AND METHOD FOR BONE FUSING IMPLANTS AND IMPLANT INSERTION TOOLS

CROSS REFERENCE TO RELATED CO-PENDING APPLICATIONS

This application claims the benefit of U.S. provisional application Ser. No. 61/878,141 filed Sep. 16, 2013 and entitled " SYSTEM AMD METHOD FOR BONE FUSING IMPLANTS AND IMPLANT INSERTION TOOLS", the contents of which are expressly incorporated herein by reference.

FIELD OF THE INVENTION

The present invention relates to a system and a method for bone fusing implants and implant insertion tools, and more particularly to bone fusing implants that are used for sacroiliac joint fusion.

BACKGROUND OF THE INVENTION

The human spine includes individual vertebras that are connected to each other. Under normal circumstances the structures that make up the spine function are configured to protect the neural structures, allow us to stand erect, bear axial loads, and are flexible for bending and rotation. Disorders of the spine occur when one or more of these spine structures are abnormal. In these pathologic circumstances, surgery may be tried to restore the spine to the normal state and to relieve the patient of pain. Spine surgery for a multitude of spinal disorders is often used for filling voids within a pathologic vertebral body (exemplified by kyphoplasty or vertebroplasty procedures), replacement of a degenerated intervertebral disc with an intervertebral implant device that preserves mobility (disc replacement) or for fusing adjacent vertebral segments (interbody and posterolateral fusions). Fusion works well because it stops pain due to movement at the joints, holds the spine in place after correcting a deformity, and prevents instability and or deformity of the spine after spine procedures such as laminectomies or verterbrectomies.

One area where fusion is applicable is for sacroiliac joint fusion (SIJF). The sacroiliac joint (SIJ) is a firm, small joint that lies at the junction of the sacrum and the pelvis. While most of the vertebras of the spine are mobile, the sacrum is made up of five vertebras that are fused together and do not move. The iliac bones are the two large bones that make up the pelvis. The sacroiliac joints connect the spine to the pelvis. The sacrum and the iliac bones are held together by a collection of strong ligaments. These joints are important in transferring the load of the upper body to the lower body, supporting the entire weight of the upper body when we are erect, which in turn results in stress to this weight-bearing area of the pelvis and spine. Pathologies of the SIJ include degenerative sacroiliitis (arthritis), sacroiliac disruption, tumors and other type of injuries. Sacroiliac joint fusion is used for treating degenerative sacroiliitis, sacroiliac disruption, and for stabilizing the SI joint after sacrectomy or after injury.

There is increasing concensus among surgeons that there is a need to develop devices, instruments, and methods to limit the size of the incision, extensive muscle stripping, prolonged retraction of muscles for visualization, avoidance of neural tissue retraction and injury, and denervation and devascularization that are known to contribute to poorer patient outcome after traditional open surgeries to treat pathologies deep within the body. In many cases these complications lead to permanent scarring and pain that can be more severe than the pain from the initial ailment. Limiting these complications in addition to the operative, general anesthesia, and recovery times are among the goals of this invention and that of percutaneous or minimally invasive surgeries.

This invention addresses the need for bone fusing implants that are used for sacroiliac joint fusion and for implant insertion tools that adhere to the principals of the less exposure surgery (LES) of outpatient surgery, which include minimizing the size of the incision, minimizing extensive muscle stripping, minimizing prolonged retraction of muscles for visualization, and preventing neural tissue refraction and injury.

SUMMARY OF THE INVENTION

The present invention relates to a system and a method for bone fusing implants and implant insertion tools, and more particularly to bone fusing implants that are used for sacroiliac joint fusion.

In general, in one aspect, the invention features a method for fusing two adjacent stacked bones including the following. First, inserting first and second pins into first and second locations of a first surface of one of the two adjacent stacked bones, respectively. Next, inserting a dilator over each of the first and second pins to dilate tissue around the first and second pins. Next, inserting a tissue protector over the dilator and removing the dilator. Next, inserting a cannulated drill through the tissue protector over each of the first and second pins and drilling first and second openings in the first and second locations, respectively, wherein the first and second opening extend through the two adjacent stacked bones. Next, tapping threads in the first opening and inserting a first bone fusing implant in the first opening, wherein the first bone fusing implant comprises threads configured to engage the threads of the first opening. Next, impacting a broach into the second opening to generate a pattern corresponding to a pattern of a second bone fusing implant and then inserting the second bone fusing implant in the second opening, and then removing the first and second pins from the first and second opening, respectively.

Implementations of this aspect of the invention may include one or more of the following features. One of the two adjacent stacked bones includes a cortical bone and the other of the two adjacent stacked bones includes a cancellous bone and the first bone fusing implant has a first segment comprising cortical threads configured to engage threads in the cortical bone and a second segment comprising cancellous threads configured to engage threads in the cancellous bone. The cortical threads are closely spaced and have larger core-to-outer diameter ratio than the cancellous threads. The cancellous threads are cut deep and are widely spaced. The first segment has a length equal to the cortical bone width and the second segment has a length equal to the cancellous bone width. The first bone fusing implant has a cylindrical hollow threaded body having a plurality of oval shaped openings and a central through-opening extending the entire length of the cylindrical hollow threaded body. The first bone fusing implant is made of bone, polyetheretherketone (PEEK), Nitinol, metals, titanium, steel, metal composites, biodegradable materials, collagen matrices, synthetic polymers, polysaccharides, calcium minerals, calcium salts, or composites containing calcium or phosphorous naturally or man made. The second bone fusing implant has a star-shaped hollow elongated body that has a central through-opening and outer ridges that are configured to engage grooves formed in an inner surface of the second opening. An outer surface of the second bone fusing implant is coated with bone growth enhancing additives and the bone growth enhancing additives comprise one of calcium phosphates, or hydroxyapatite. The first and second pins are inserted into the first and second locations of the first surface of one of the two adjacent stacked bones via a pin guide tool and the pin guide tool is configured to set relative position, distance, pin depth and pin orientation of the first and second pins. The pin guide tool includes a main body, and a pin alignment slide and the main body has an upper portion and a lower portion and the upper portion extends along a first direction perpendicular to the lower portion and has a cylindrical through-opening shaped and dimensioned to slidably receive the first pin, and the pin alignment slide has a cylindrical through-opening extending parallel to the cylindrical through-opening of the upper portion and being shaped and dimensioned to slidably receive the second pin. The upper portion of the main body includes markings indicating the diameter of the first bone fusing implant and the pin alignment slide includes markings indicating the diameter of the second bone fusing implant. The pin alignment slide includes a through-slot shaped and dimensioned to slidably receive the lower portion of the main body and the pin alignment slide is configured to set the distance between the first and second pins by sliding along the lower portion of the main body in a direction perpendicular to the first direction. The lower portion of the main body includes a slide with teeth and the pin alignment slide is configured to slide along the slide and the position of the pin alignment slide is secured along the slide by engaging a lever. The dilator includes a cylindrical body with a central through-opening shaped and dimensioned to slide over the first and second pins, and the cylindrical body of the dilator includes a segment with recessed parallel surfaces, curved upper and lower edges and a depth marker. The tissue protector includes a tubular hollow cylindrical body having a proximal end and an angled distal end and the angled distal end includes teeth and the proximal end includes a ring-shaped surface surrounding a lumen and includes the lumen has first and second opposite alignment channels. The tissue protector further includes an elongated detachable handle and a table mount ring extending from an edge of the ring-shaped surface and the elongated detachable handle is configured to be attached to locations around the ring-shaped surface. The broach includes an elongated cylindrical body having an impaction area at a proximal end and alignment pins at a distal end and the broach further includes a tissue tapping end effector configured to be removably attached to the distal end. The impaction area has a flat top surface and a side notch. The tissue tapping end effector includes outer cutting surfaces configured to generate the pattern of the second bone fusing implant in the second opening. The elongated cylindrical body includes a curved channel formed along a side surface of the elongated cylindrical body and being configured to receive a guide wire and the curved channel is aligned with the side notch of the impaction area. The tissue tapping end effector comprises a through-opening configured to receive the guide wire. The cylindrical body further comprises depth markers configured to indicate a tapping depth. The first and second bone fusing implants are inserted with an implant inserter tool and the implant inserter tool comprises an elongated cylindrical body, a handle, an impaction area, alignment pins and an implant holder and the impaction area is located at a proximal end of the elongated cylindrical body and the implant holder is attached to a distal end of the elongated cylindrical body and the implant holder comprises structures configured to engage corresponding structures on a proximal end of the first and second bone implants.

The details of one or more embodiments of the invention are set forth in the accompanying drawings and description below. Other features, objects, and advantages of the invention will be apparent from the following description of the preferred embodiments, the drawings, and the claims

BRIEF DESCRIPTION OF THE DRAWINGS

Referring to the figures, wherein like numerals represent like parts throughout the several views.

DETAILED DESCRIPTION OF THE INVENTION

The present invention relates to a system and a method for bone fusing implants and implant insertion tools, and more particularly to bone fusing implants that are used for sacroiliac joint fusion.

Figure 1:
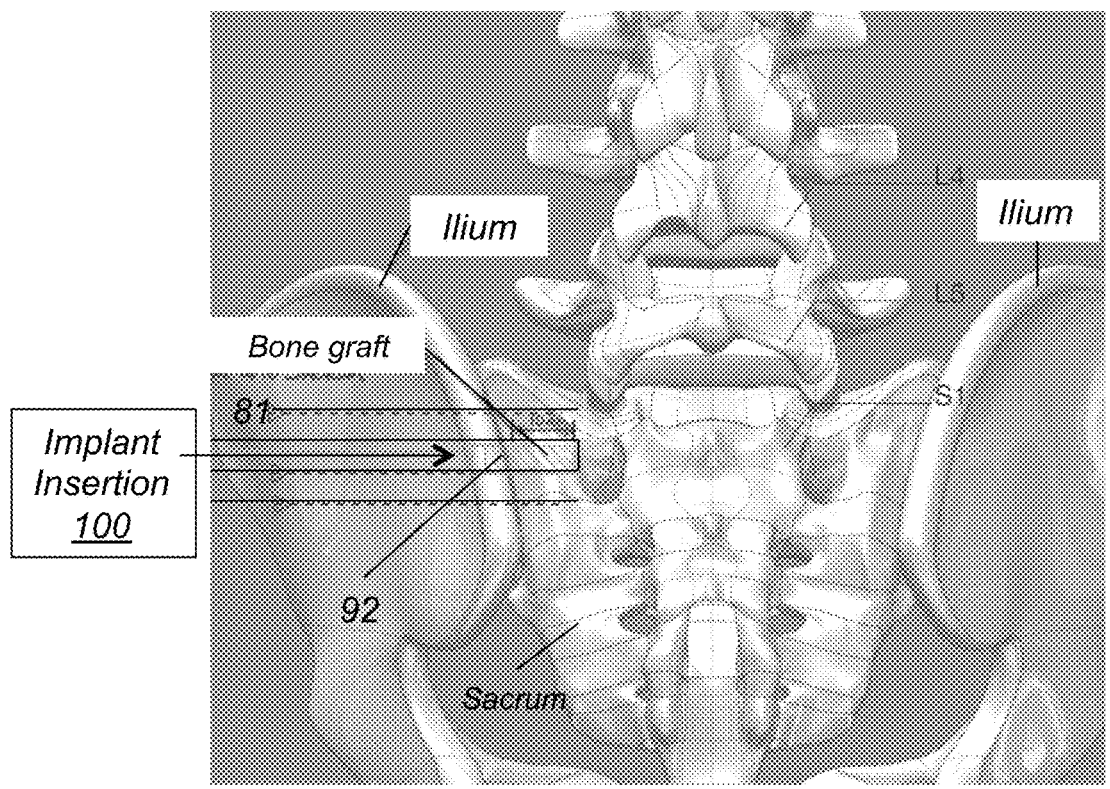
FIG. 1 is a schematic anterior view of the pelvic bones and sacrum.
Figure 1A:
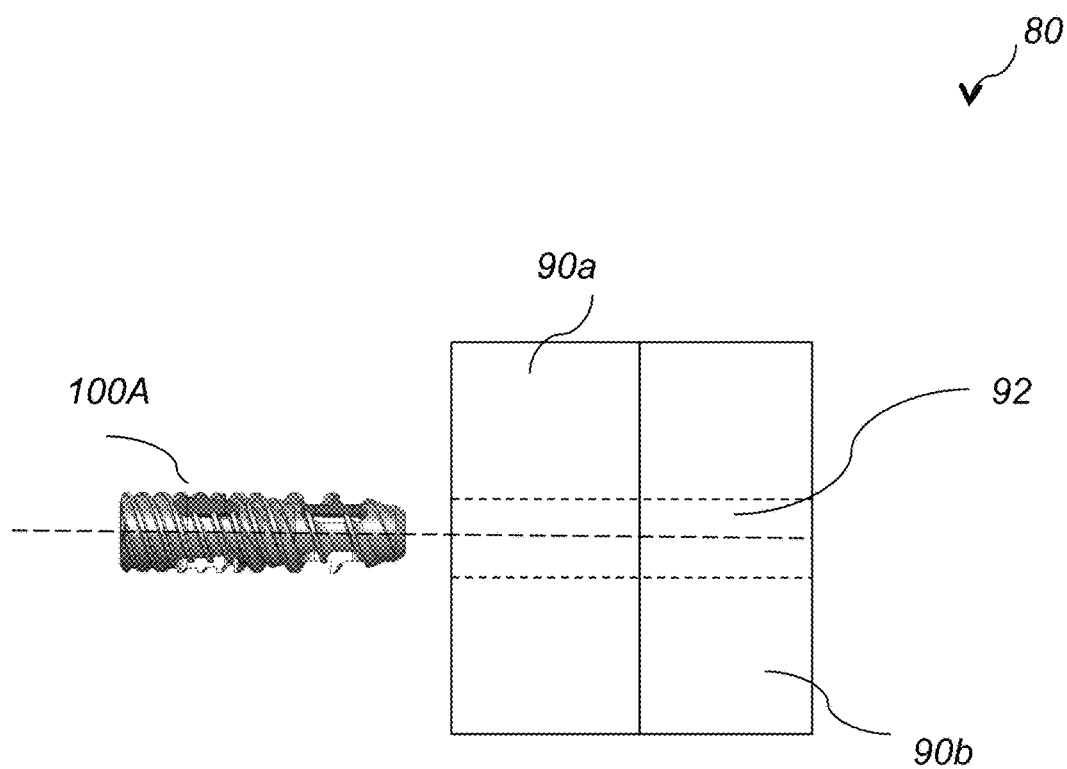
FIG. 1A is a schematic side view of a an embodiment of a bone fusing implant that is used for fusing two adjacent bones, according to this invention.
Figure 1B:
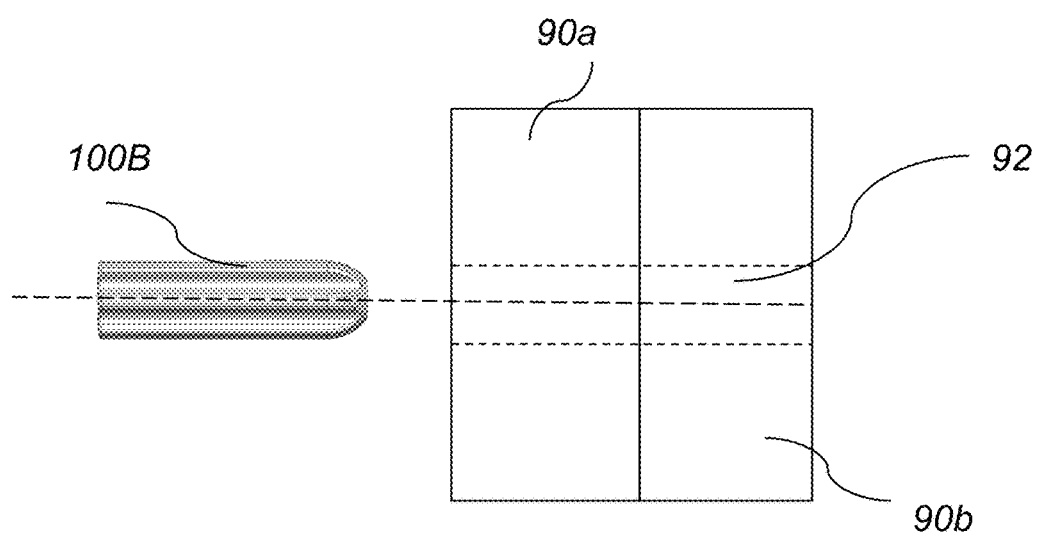
FIG. 1B is a schematic side view of another embodiment of a bone fusing implant that is used for fusing two adjacent bones, according to this invention.
Figures 2A, 2B:
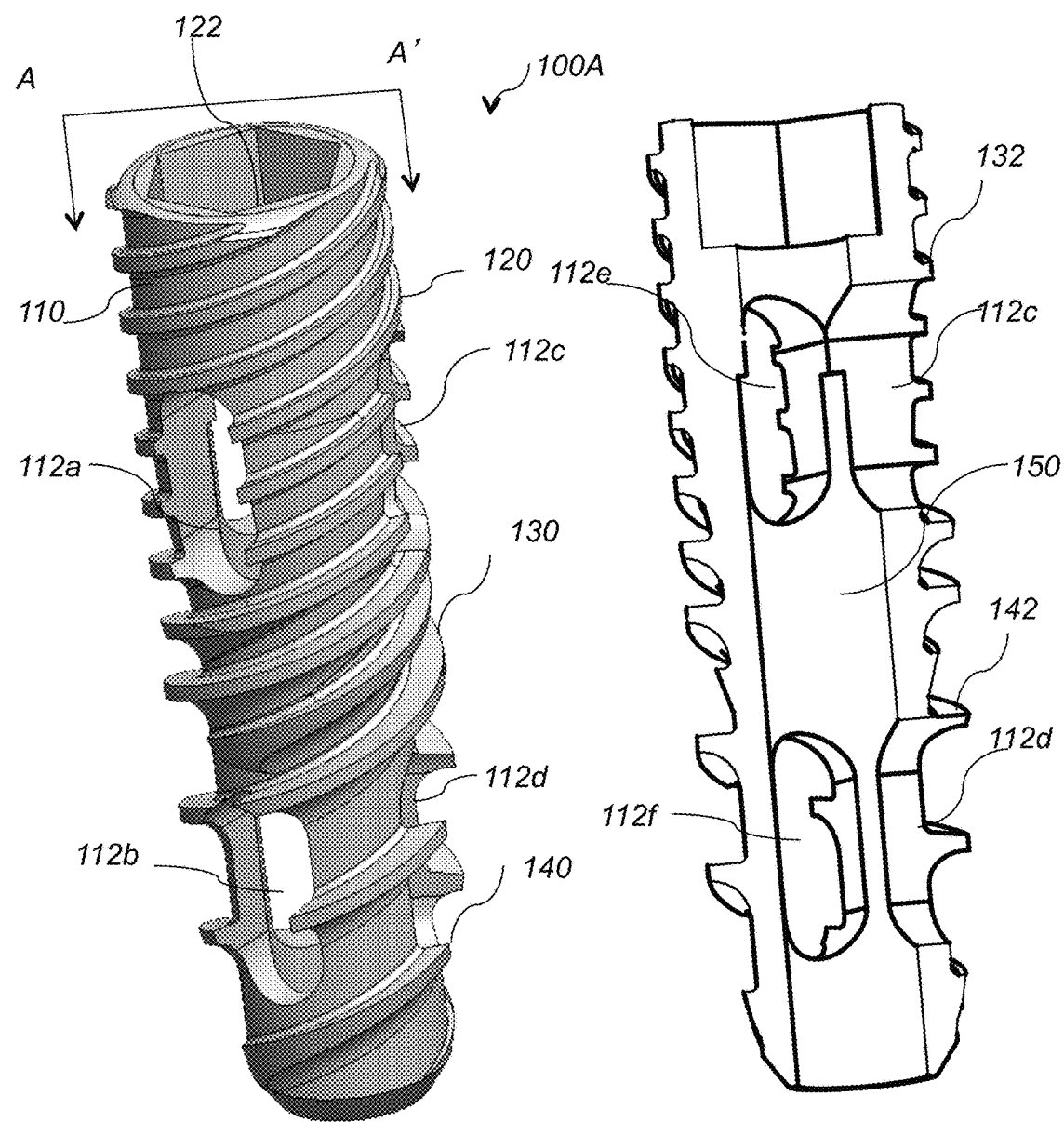
FIG. 2A is a perspective view of a bone fusing implant.
FIG. 2B is a cross-sectional view of the bone fusing implant of FIG. 2A along plane A-A'.
Figure 3:
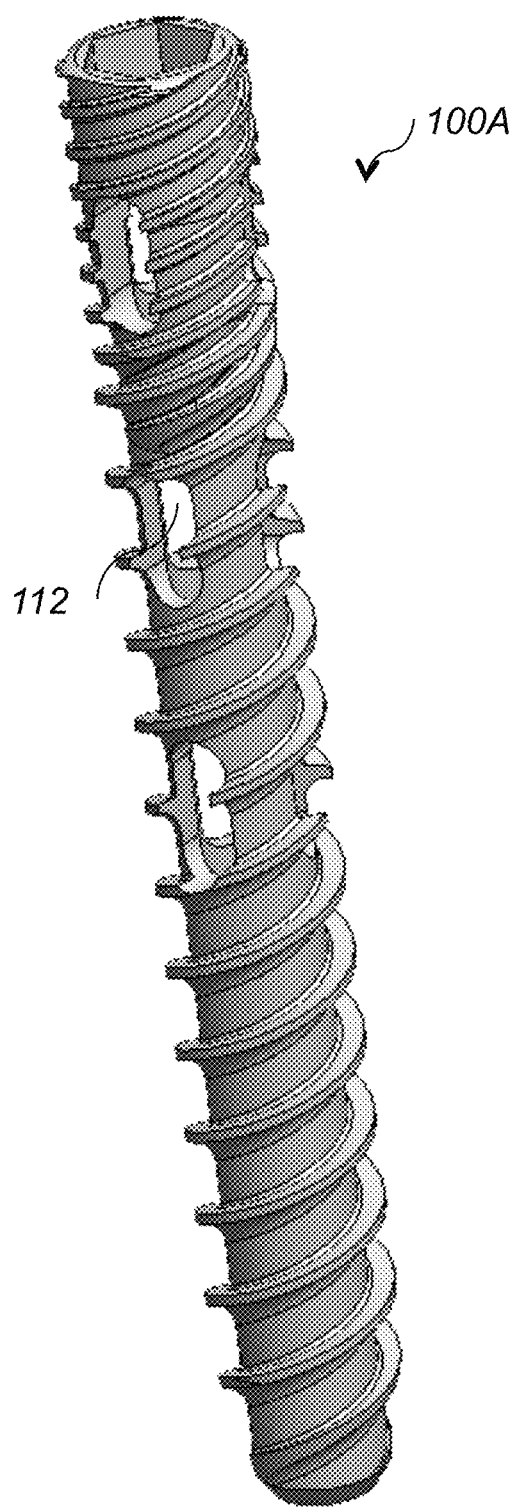
FIG. 3 is a perspective view of another example of the bone fusing implant of FIG. 2A.

Referring to FIG. 1, in SIJF surgery one or more openings 92 are formed along the arrow direction 81 and bone fusing implants 100 are inserted in the formed openings 92. Referring to FIG. 1A, bone fusing implant 100A is inserted in opening 92 that is formed through two stacked adjacent bone members 90a and 90b. In one example, bone member 90a is primarily a cortical (compact) bone and bone member 90b is in majority a cancellous (porous) bone. Referring to FIG. 2A and FIG. 2B, bone implant 100A includes a cylindrical hollow threaded body 110 that has six oval shaped openings 112a, 112b, 112c, 112d, 112e, 112f, a through opening 122 that extends the entire length of the implant and a first segment 130 with cortical threads 132 and a second segment 140 with cancellous threads 142. Cortical threads 132 are closely spaced and have larger core-to-outer diameter ratios than cancellous threads. Screws with cortical threads are used for fixation of cortical (compact) bone. Cancellous threads 142 are cut deep and are widely spaced. Screws with cancellous threads are designed for fixation of cancellous (porous) bone. Since cancellous bone is much less dense than cortical bone, the screw threads cut their path in the bone when the screw is inserted, i.e. cancellous screws are self-tapping. In one example, implant 100A has a length of 35 mm and a diameter of 12 mm. The segment 130 with the cortical threads 132 has a length of 15 mm, which corresponds to the width of the cortical bone 90a. The segment 140 with the cancellous threads 142 has a length of 20 mm, which corresponds to the width of the cancellous bone 90b. Through-opening 122 and oval shaped openings 112a, 112b, 112c, 112d, 112e, 112f are used for inserting graft material into the graft area 150. In other examples, bone implant 100A, has a length of 60 mm and includes nine oval-shaped openings 112, as shown in FIG. 3. Bone implant 100A is made of bone, polyetheretherketone (PEEK), Nitinol, metals, titanium, steel, metal composites, biodegradable materials, collagen matrices, synthetic polymers, polysaccharides, calcium minerals, calcium salts, or composites containing calcium or phosphorous naturally or man made.

Figures 4A, 4B:
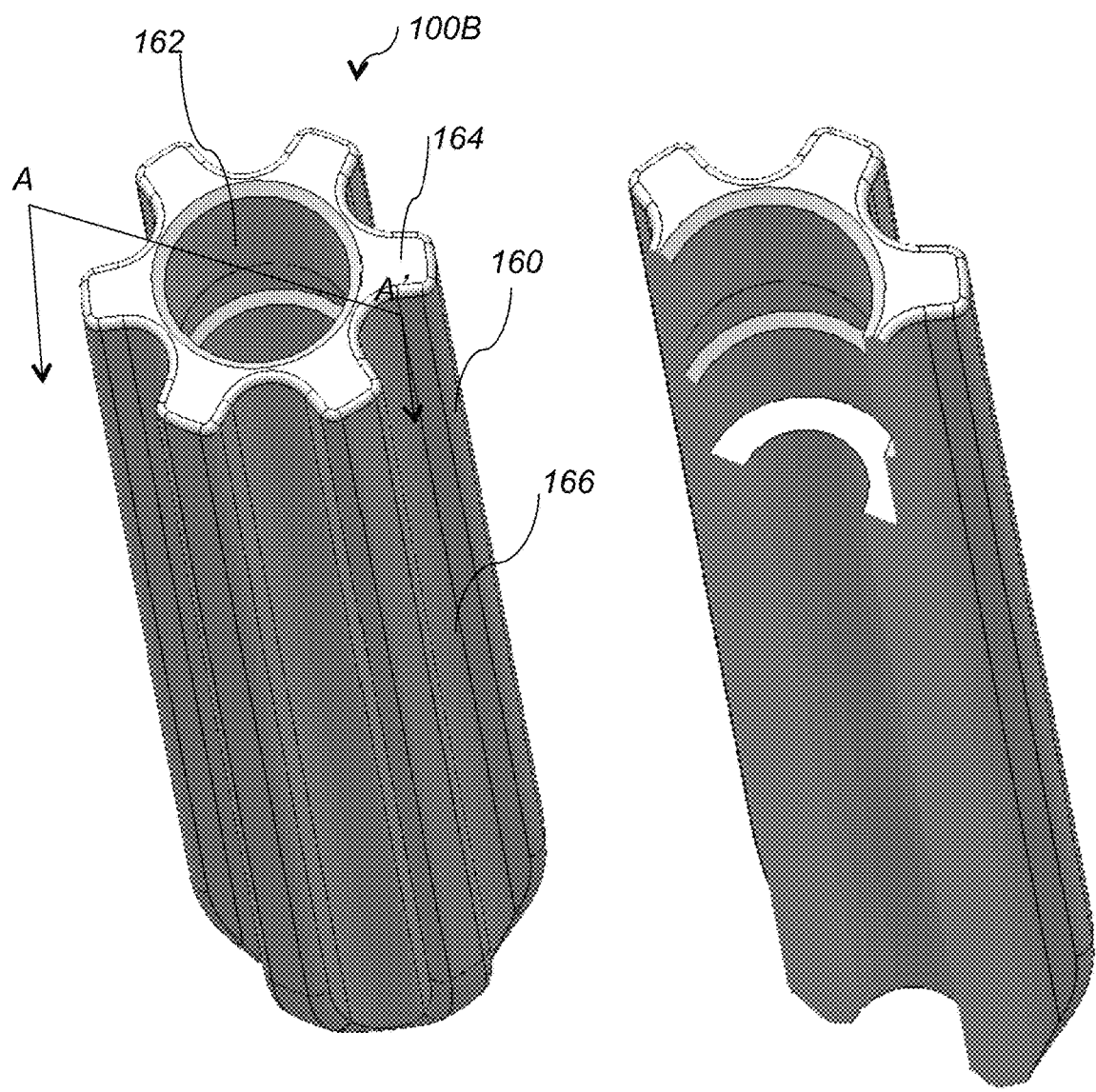
FIG. 4A is a perspective view of another embodiment of the bone fusing implant, according to this invention.
FIG. 4B is a cross-sectional view of the bone fusing implant of FIG. 4A along plane A-A'.

In another embodiment, bone implant 100B includes a star-shaped hollow elongated body 160 that has a through opening 162 and outer ridges 166, as shown in FIG. 4A and FIG. 4B. The star-shaped elongated body 160 provides increased surface area due to the surface areas provided by ridges 166. The increased surface area contributes to better joint fixation, which minimizes micro-motion and therefore improves bone fusion. In one example, implant 100B has a length of 45 mm, a diameter of 15.5.mm and is made of a titanium rod. The outer surface of the implant may be coated with bone growth enhancing additives such as calcium phosphates, hydroxyapatite, or similar, which provides a textured porous surface. The implant is coated via plasma evaporation of electron beam melting.

Figure 5:
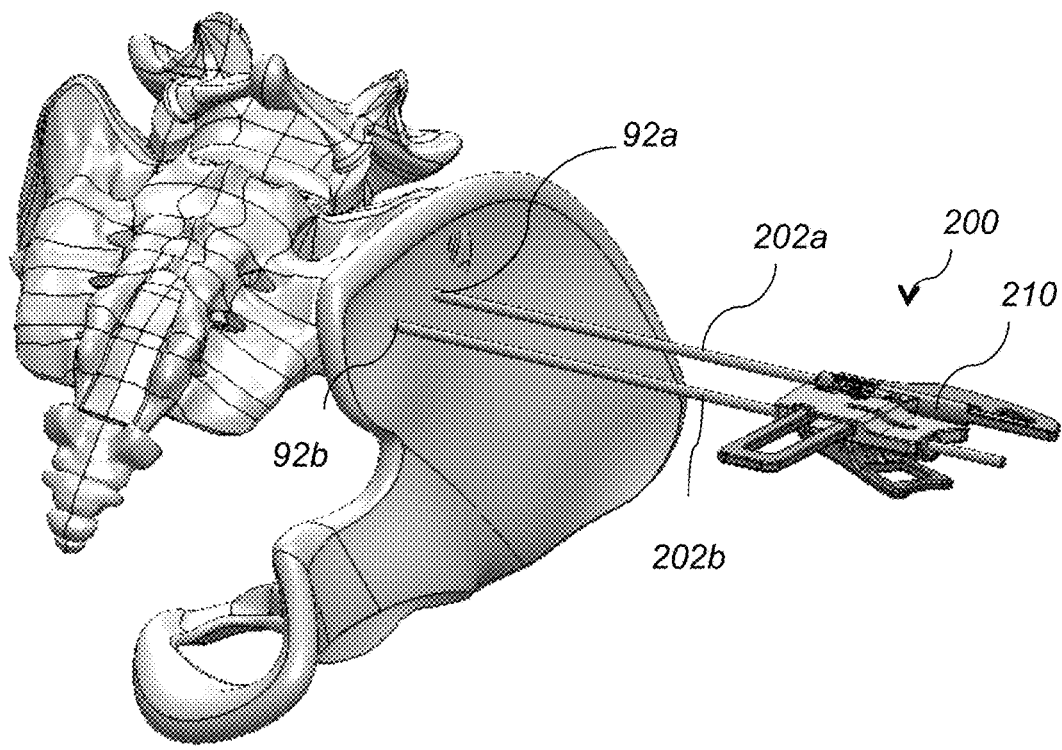
FIG. 5 is a perspective view of a pin guide used to insert pins into the pelvic bones and sacrum.
Figure 6:
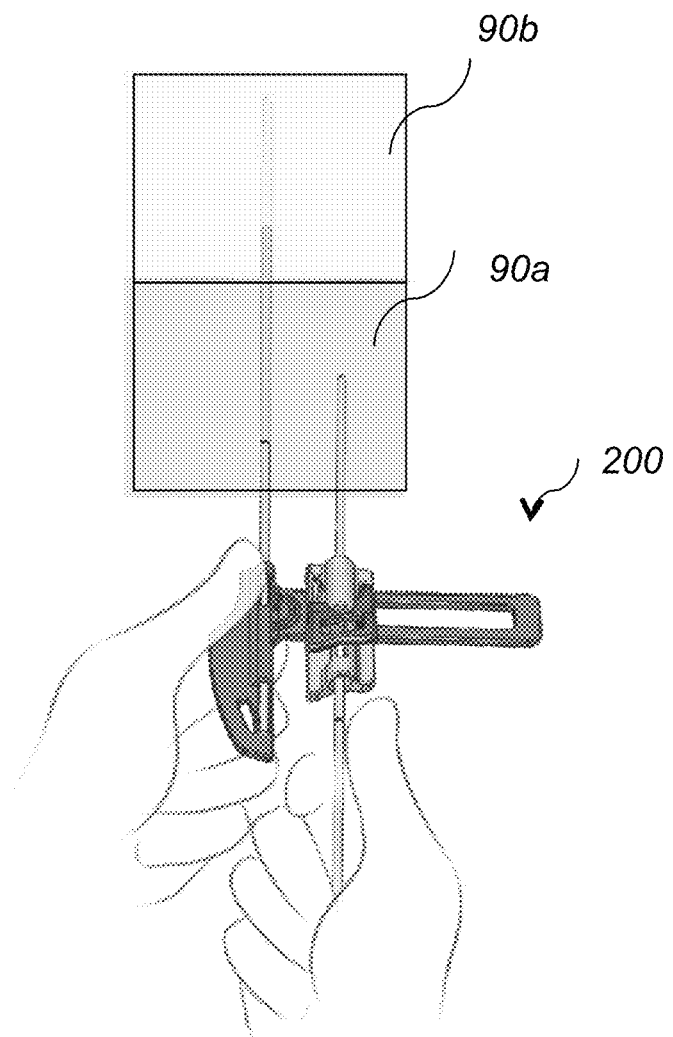
FIG. 6 is a schematic side view of the pin guide of FIG. 5 used to insert pins into two adjacent stacked bones.
Figure 7:
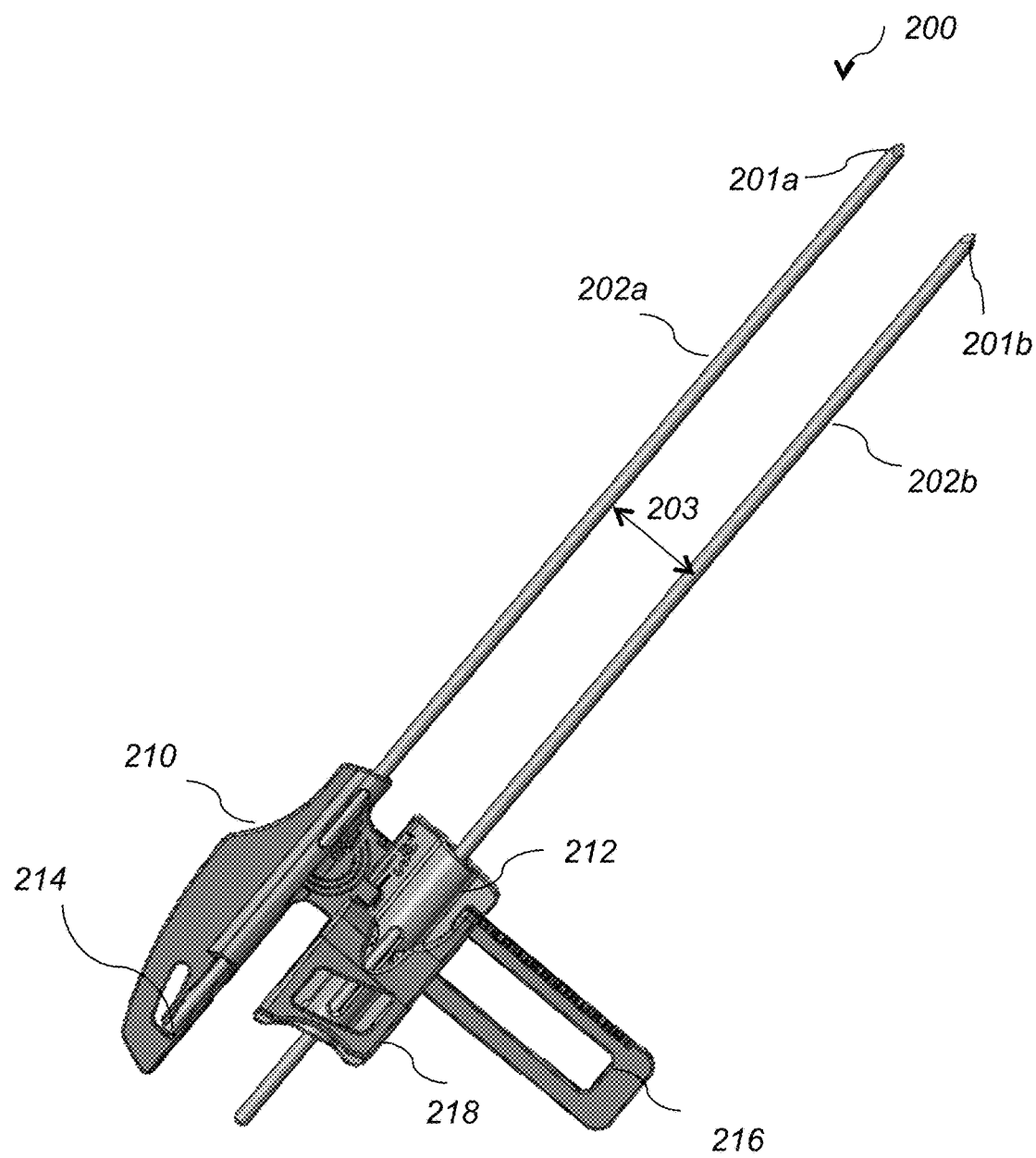
FIG. 7 is a side view of the pin guide of FIG. 5.
Figure 8:
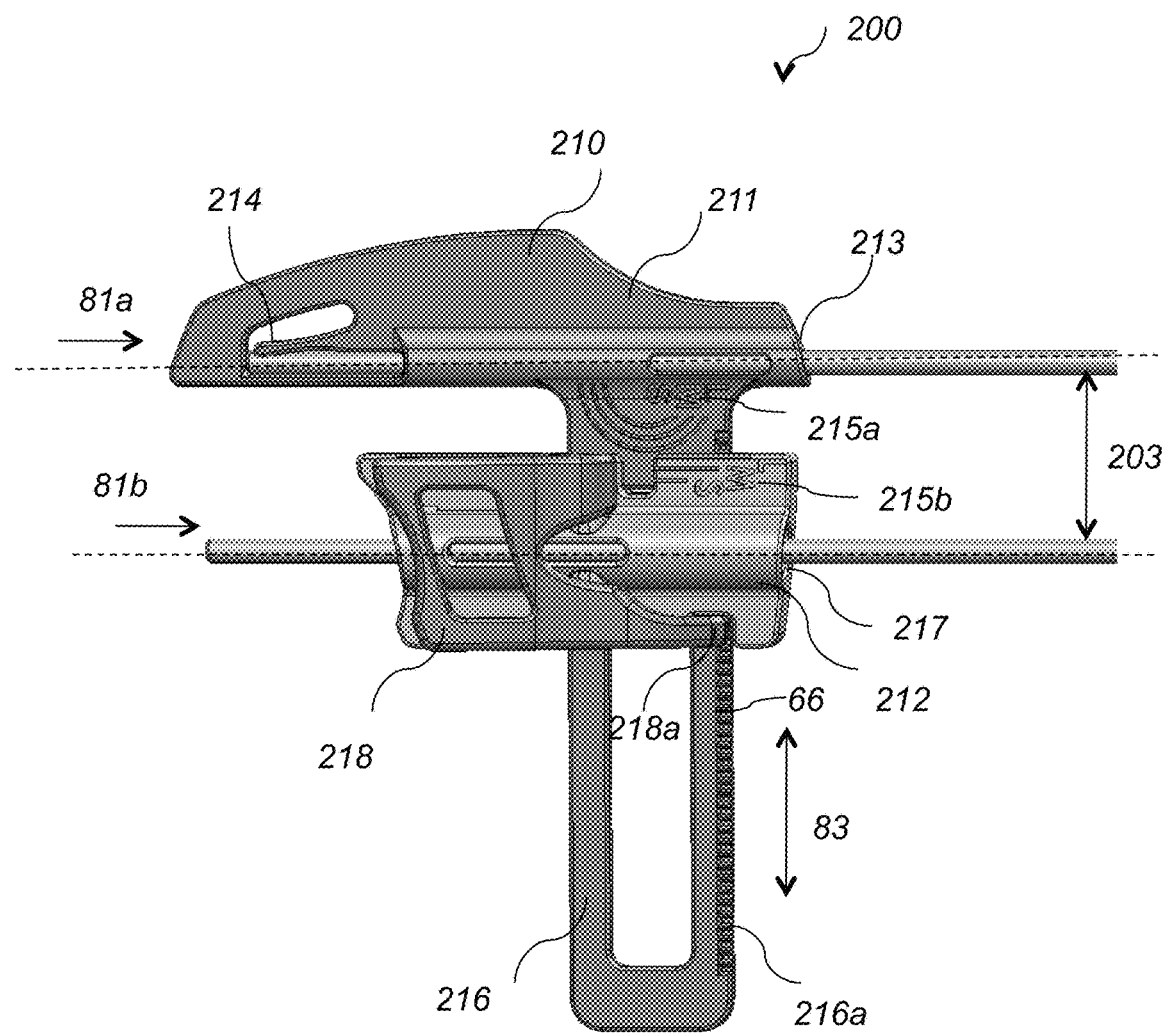
FIG. 8 is an enlarged side view of the pin guide of FIG. 5.
Figure 9:
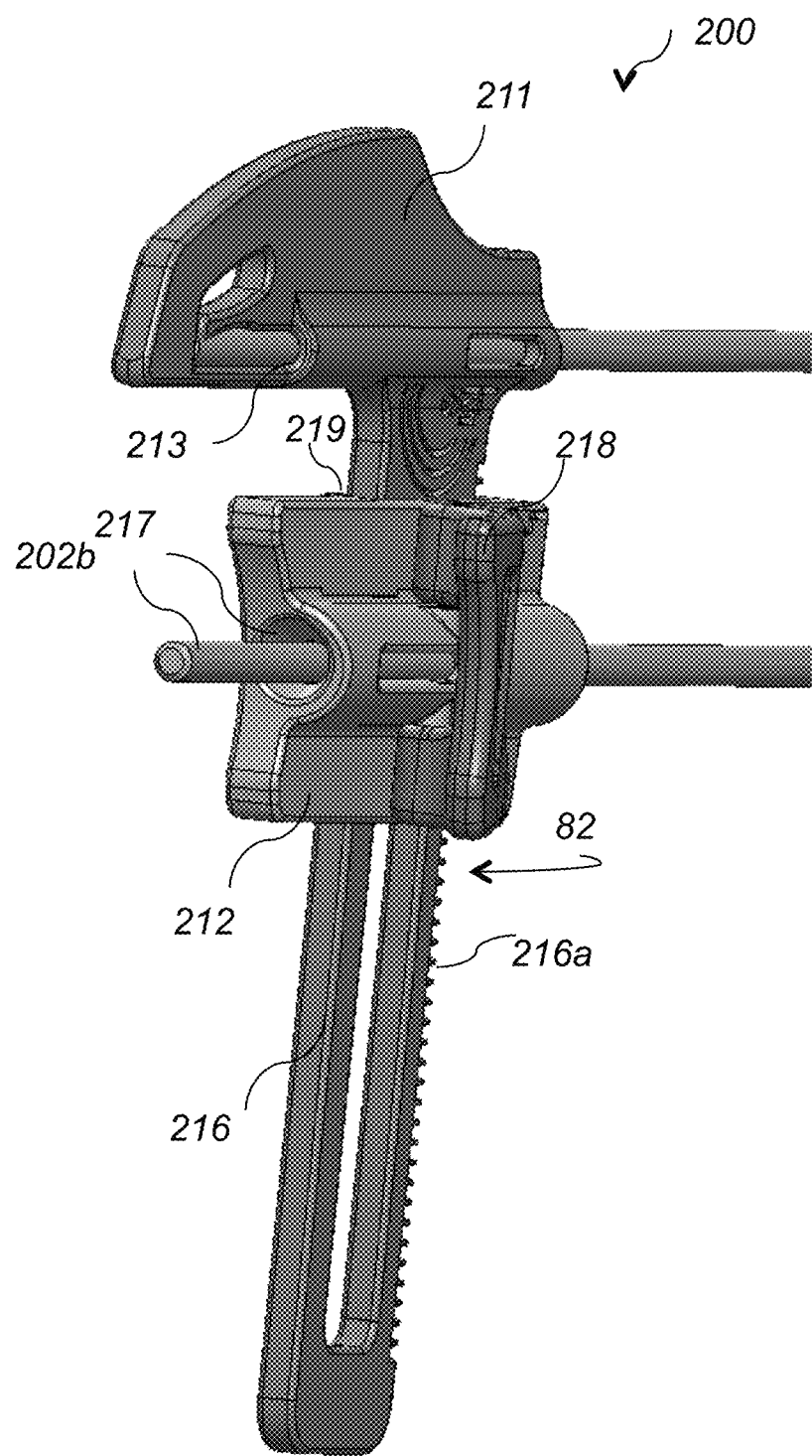
FIG. 9 is an enlarged perspective view of the pin guide of FIG. 5.
Figures 10A, 10B:
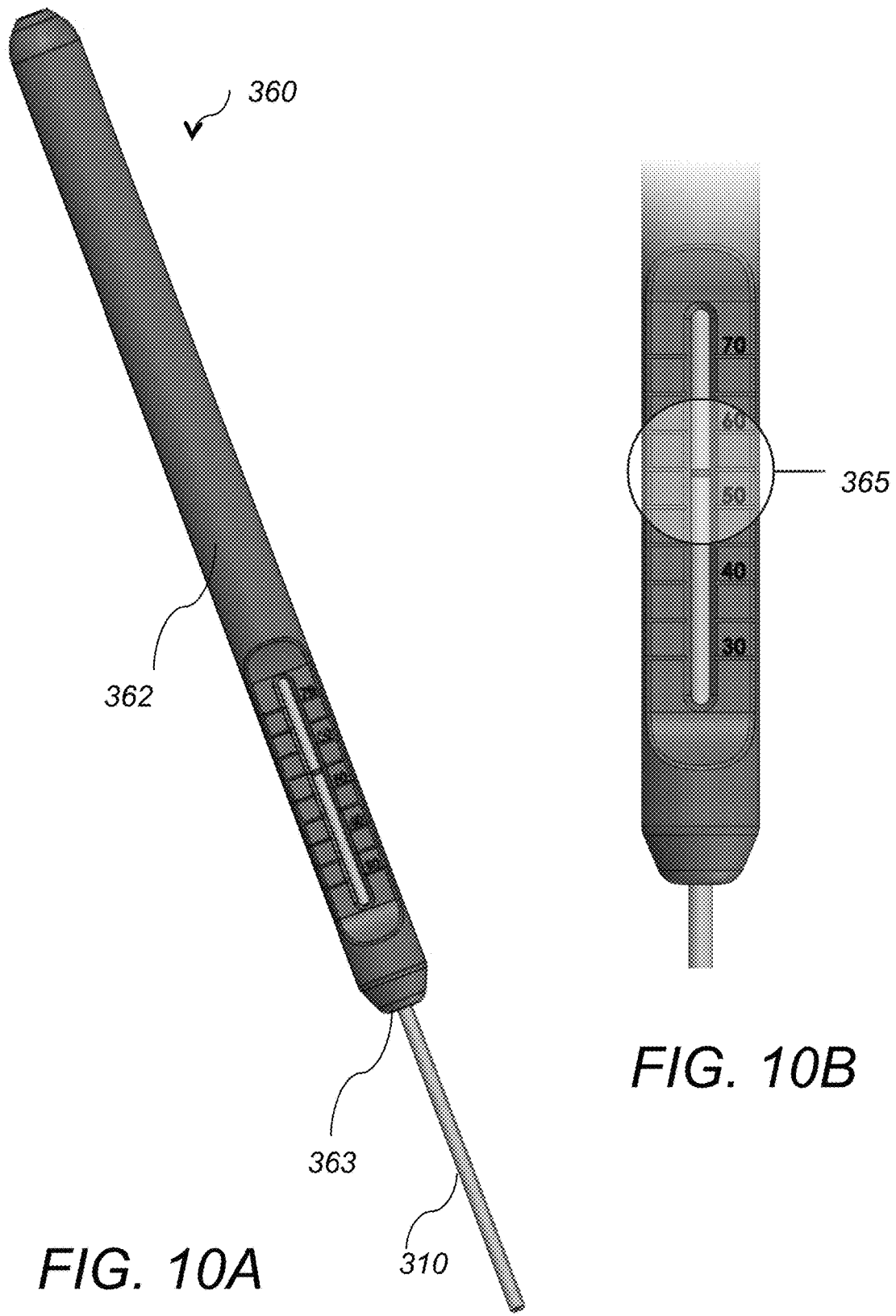
FIG. 10A is a perspective view of a dilator tool.
FIG. 10B is an enlarged front view of the dilator of FIG. 10A.
Figures 11A, 11B:
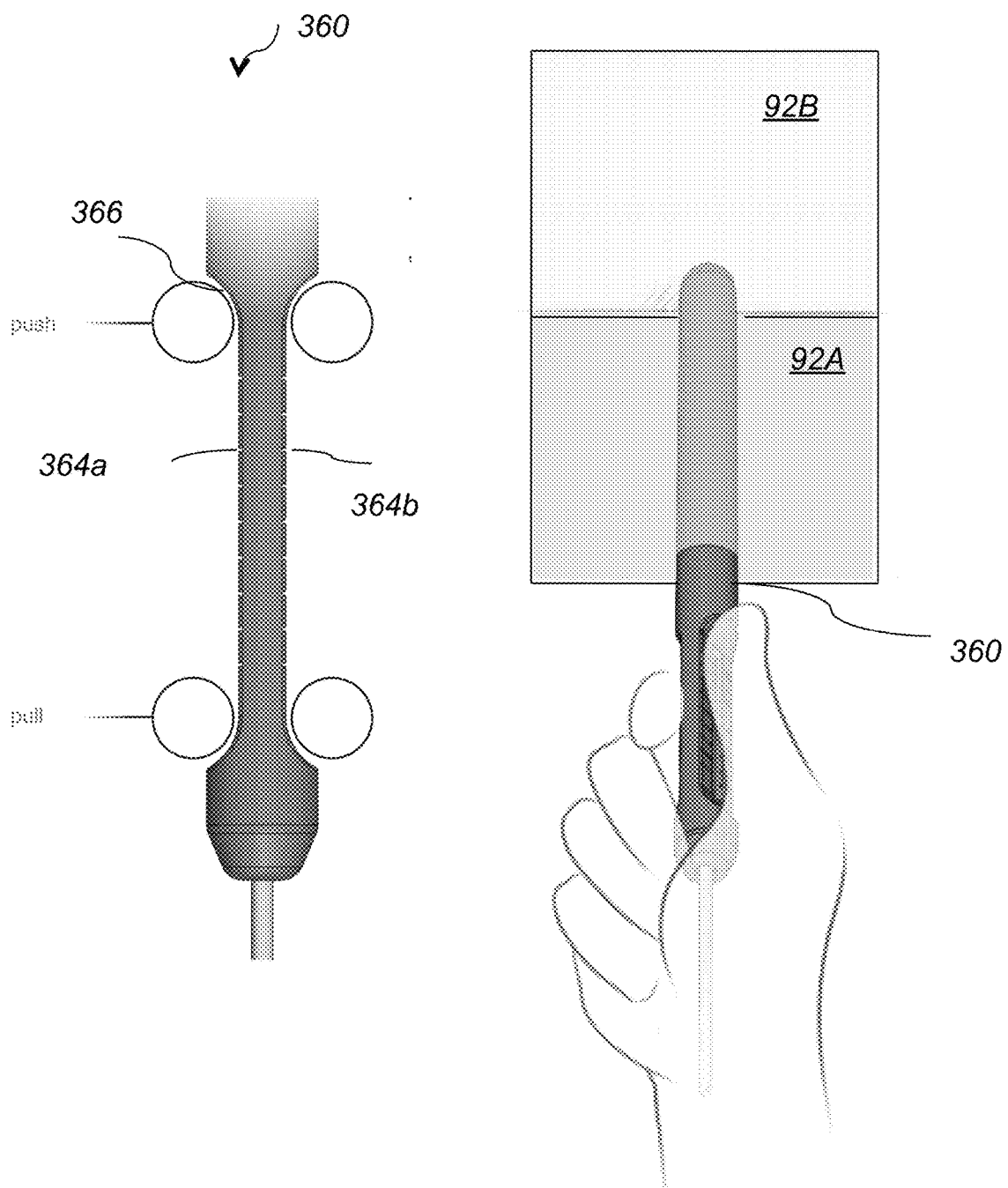
FIG. 11A is an enlarged side view of the dilator of FIG. 10A.
FIG. 11B is a schematic perspective view of the dilator of FIG. 10A inserted through two adjacent stacked bones.

Bone fusing implants 100A or 100B are inserted into openings formed through the ilium and the adjacent sacrum. Referring to FIG. 5 (or FIG. 6), openings 92a, 92b are formed through the ilium and the adjacent sacrum (or through stacked adjacent bones 90a, 90b) by inserting pins 202a, 202b via a pin guide tool 200. The relative position, distance, pin depth and orientation of pins 202a, 202b is set by the pin guide 200. Referring to FIG. 7, FIG. 8 and FIG. 9, pin guide 200 includes a main body 210, a pin alignment slide 212 and a release lever 218. Main body 210 includes an upper portion 211 and a lower portion 216. Upper portion 211 extends along direction 81a, perpendicular to the lower portion 216 and has a cylindrical opening 213 that extends along the upper portion 211 and is dimensioned to slidably receive pin 202a. Below opening 213 there are markings 215a (S, M, L) indicating the diameter of the implant used. The markings include small (S), medium (M), and large (L). Upper portion 211 also includes a pin lock 214 that secures the position of pin 202a within opening 213. Lower portion 216 extends perpendicular to direction 81a and includes a side 216a with teeth 66. Pin alignment slide 212 includes a through-slot 219 that is shaped and dimensioned to slidably receive the lower portion 216 of the main body 210. Pin alignment slide 212 also includes a cylindrical opening 217 that extends parallel to opening 213 and is dimensioned to slidably receive pin 202b. Pin alignment slide 212 slides around the lower portion 216 along direction 83 and sets the relative distance 203 between pins 202a, 202b. Above opening 217 there are markings 215b (S, M, L) indicating the distance between pins 202a and 202b. The markings include small (S), medium (M), and large (L). The position of pin alignment slide 212 relative to the main body 210 is secured by engaging the lever tip 218a with teeth 217 along side 216a of the lower portion 216. Pressing the release lever 218 along direction 82 towards the pin alignment slide 212 disengages the lever tip 218a from teeth 66, releases the pin alignment slide 218 and allows it to slide around the lower portion 216 along direction 83.

After the insertion of pins 202a, 202b, the openings 92a, 92b are dilated with dilator 360, shown in FIG. 10A-FIG. 11B. Dilator 360 includes a cylindrical body 362 with a through opening 363 and recessed parallel surfaces 364a, 364b. Opening 363 is dimensioned so that the dilator slides over the inserted pins 310. Recessed surfaces 364a, 364b have curved upper and lower edges 366. Curved edges 366 are used to push against or pull against them in order to advance the dilator 360 forward or backward. Recessed surfaces 364a, 364b also include a depth marker 365 that indicates the bone implant length. In the example of FIG. 10B, the bone implant length is 55 mm.

Figure 12:
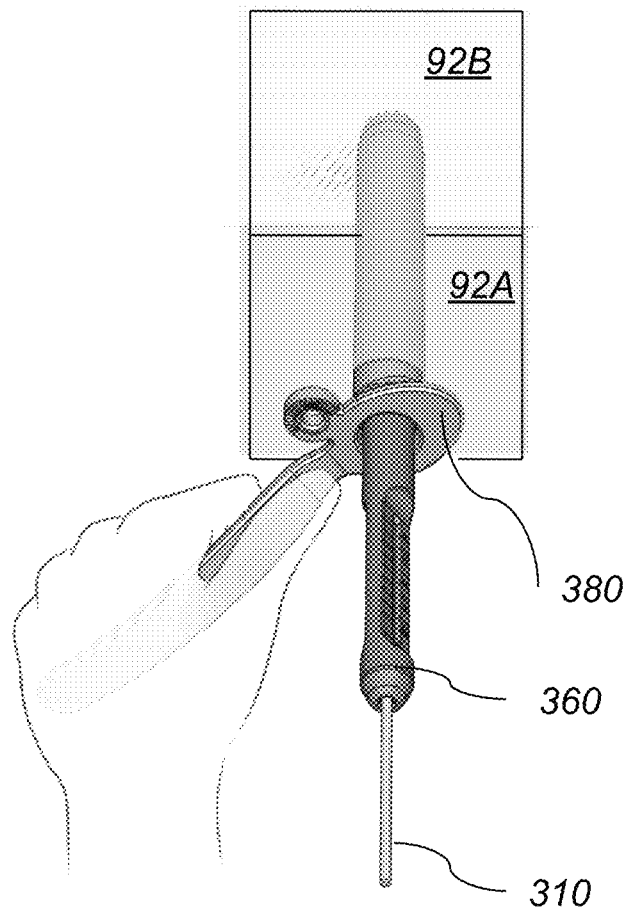
FIG. 12 is a schematic perspective view of a tissue protector inserted through two adjacent stacked bones.
Figures 13A, 13B:
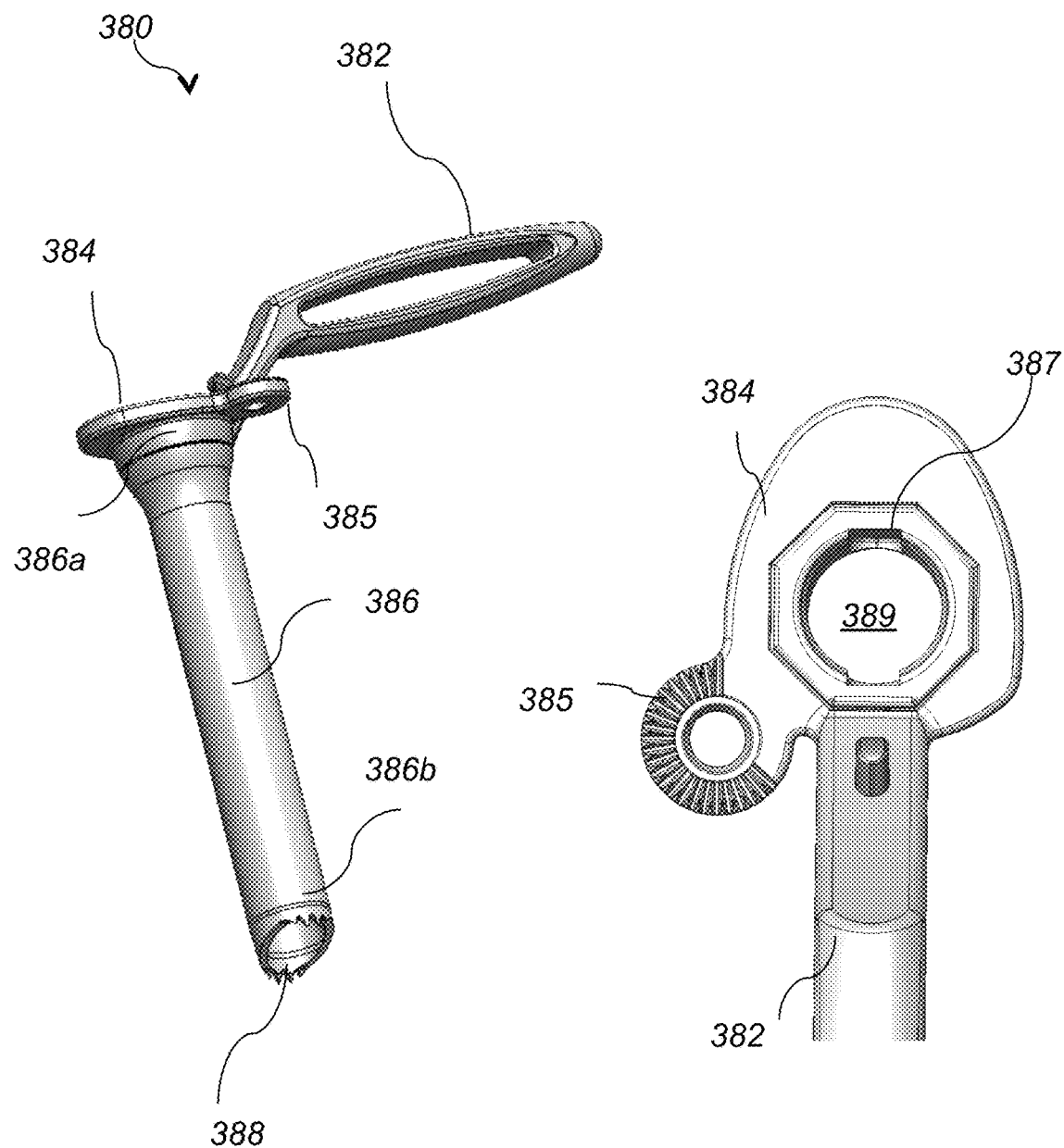
FIG. 13A is a side view of the tissue protector of FIG. 12.
FIG. 13B is a partial top view of the tissue protector of FIG. 12.

Dilator 360 is inserted into openings 92a, 92b, through a tissue protector 380, as shown in FIG. 12. Referring to FIG. 13A and FIG. 13B, tissue protector 380 includes a tubular hollow cylindrical body 386 that has aggressive teeth 388 at its distal end 386b. Distal end 386b includes an angled distal tip that conforms to the ilium from a lateral trajectory. The proximal end 386a of the cylindrical body 386 includes a ring-shaped surface area 384 surrounding lumen 389. Lumen 389 includes opposite alignment channels 387 that are used to keep instruments that are inserted through the lumen aligned. Alignment channels 387 don't run all the way through the guide, and end about 10 mm from the distal end. A table mount ring 385 extends from an edge of surface area 384. An elongated handle 382 extends sidewise from an edge of the surface area 384, as well. Handle 382 is used for holding the tissue protector 380. Handle 382 is detachable and can be repositioned to a desired location at 8 preset angles. Other tools that are inserted through the tissue protector 380 include implant inserters 250, broaches 300 and impactors 340.

Figure 14:
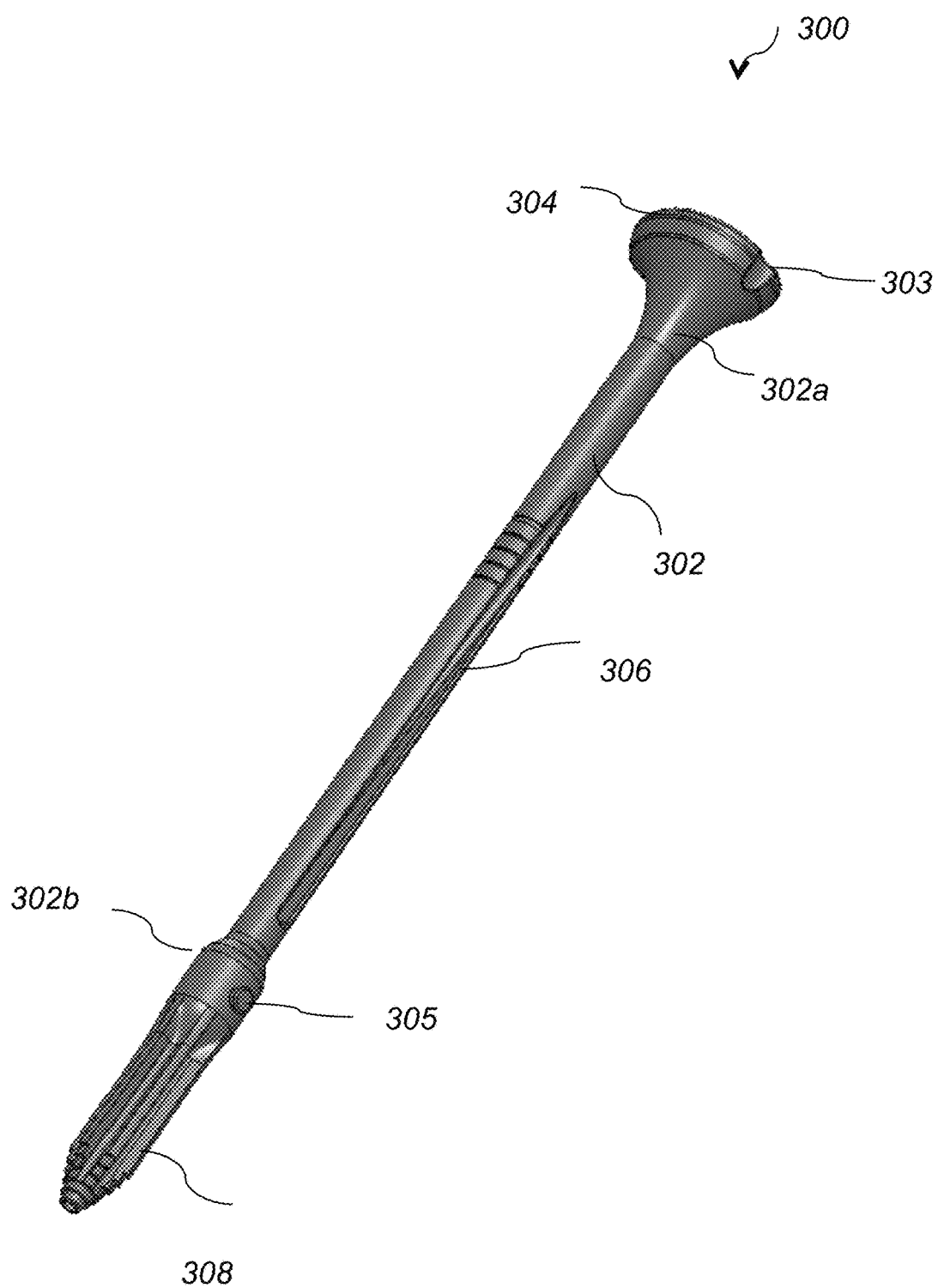
FIG. 14 is a perspective view of one example of a broach tool, according to this invention.
Figure 15:
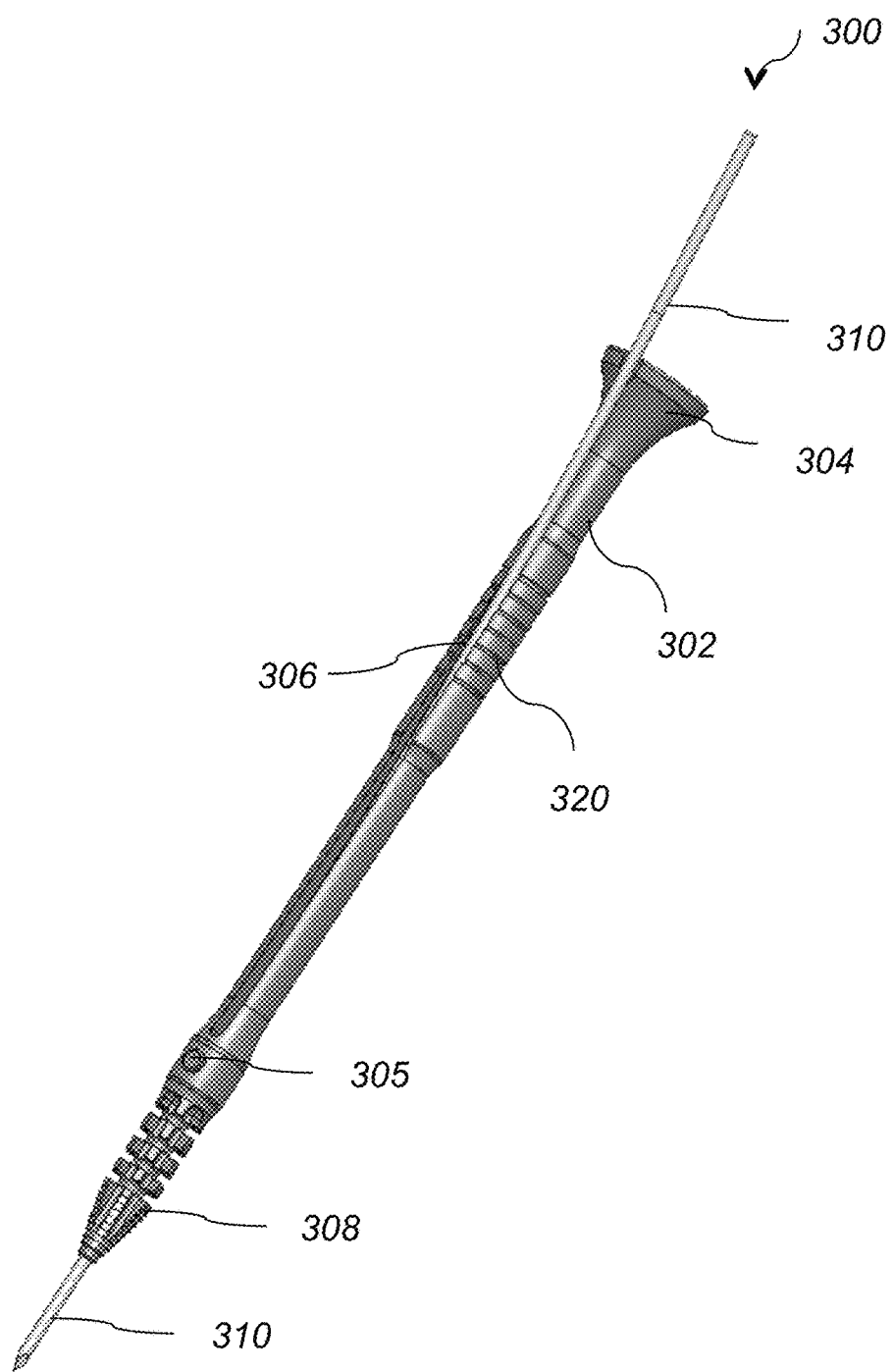
FIG. 15 is a perspective view of another example of a broach tool, according to this invention.

Referring to FIG. 14, a broach tool 300 includes an elongated cylindrical body 302 that includes an impaction area 304 at the proximal end 302a and alignment pins 305 at the distal end 302b. Alignment pins 305 interface with the alignment channels 387 of the tissue protector 380. Impaction area 304 is flat and includes a notch 303. Tissue tapping end effectors 308 are removably attached to the distal end 302b. Tissue tapping end effectors 308 have outer cutting surfaces with various shapes, as shown in FIG. 14 and FIG. 15, and a through opening that is dimensioned to receive the guide wire 310. Guide wire 310 is inserted into the through opening of the end effector 308 via a curved guide wire channel 306 that is formed along the side of the elongated cylindrical body 302. Channel 306 is aligned with notch 303. Channel 306 is shaped and dimensioned to receive the guide wire so that the guide wire is curved away from the impaction surface 304 and away from the user. Cylindrical body 302 also includes a depth marker 320 that indicates the tapping depth.

Figure 16:
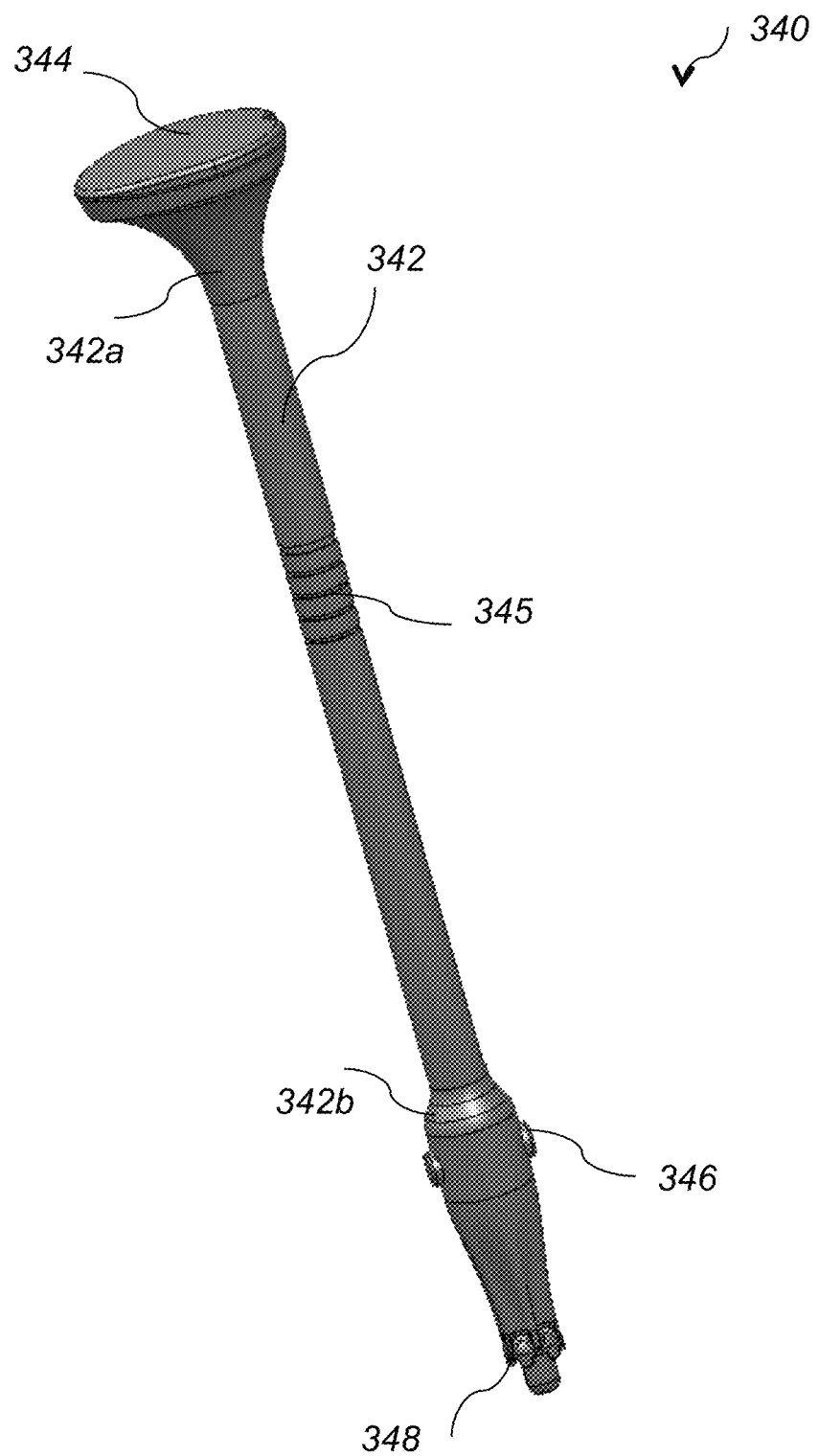
FIG. 16 is a perspective view of one example of an impactor tool, according to this invention.
Figures 16A, 16B:
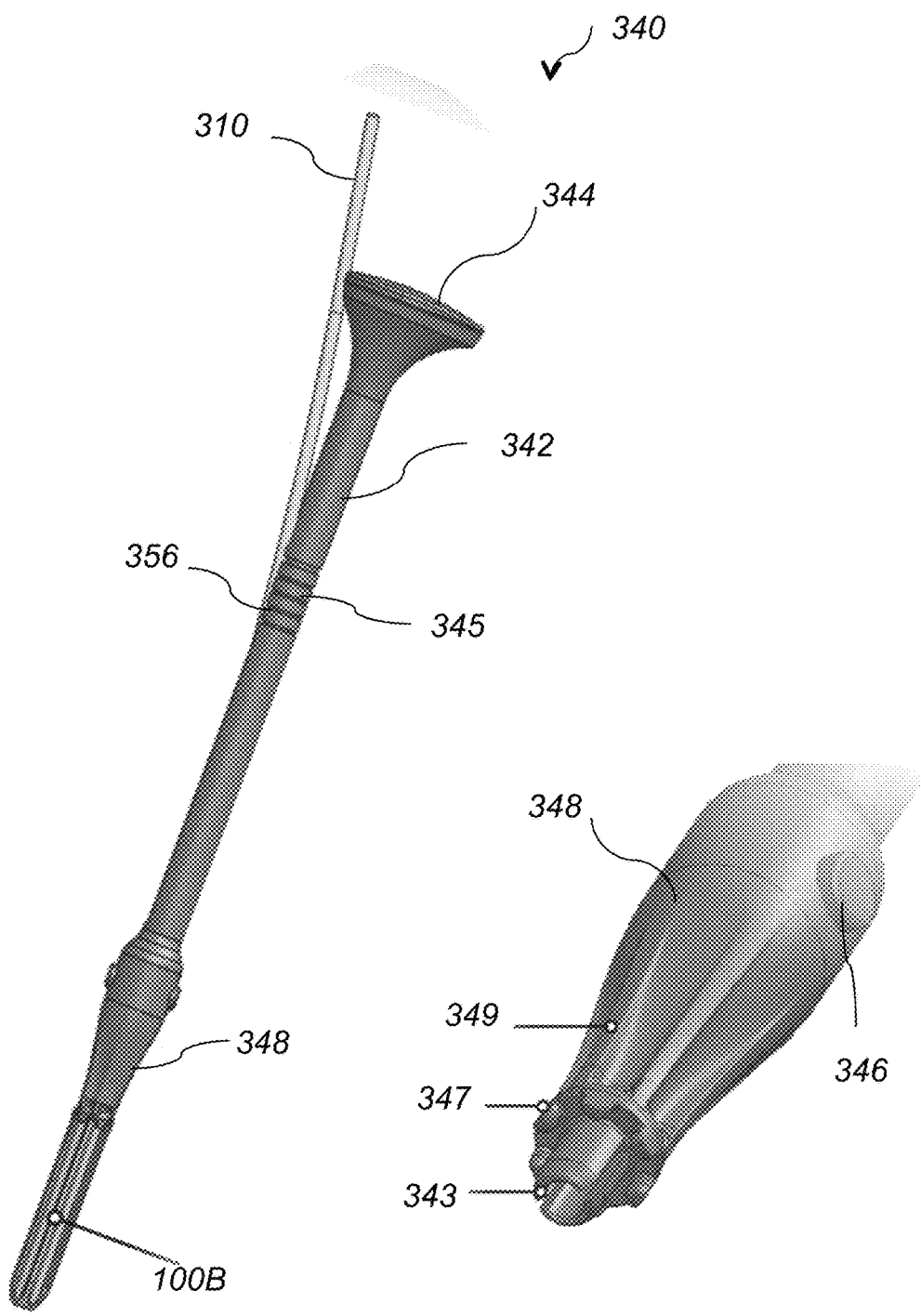
FIG. 16A is a perspective view of the impactor tool of FIG. 16 holding the bone fusing implant of FIG. 4A.
FIG. 16B is an enlarged implant holder tip of the impactor tool of FIG. 16.

Referring to FIG. 16, FIG. 16A and FIG. 16B, impactor tool 340 includes an elongated cylindrical body 342 that includes an impaction area 344 at the proximal end 342a and an impactor tip 348 at the distal end 342b. Impactor tip 348 is used for holding and impacting a bone implant 100B into a tissue opening. Impactor tip 348 includes alignment pins 346, alignment ribs 349, implant anti-rotation features 347 and friction fit implant holder 343, as shown in FIG. 16B. Alignment pins 346 interface with the alignment channels 387 of the tissue protector 380. Implant 100B is removably attached to the friction fit implant holder 343 and the implant anti-rotation features interface with the star-shaped structure in the top of the implant 100B. Guide wire 310 is inserted into the through opening of the implant 100B via a curved guide wire channel 356 that is formed along the side of the elongated cylindrical body 342. Channel 356 is shaped and dimensioned to received a guide wire so that the guide wire is curved away from the impaction surface 344 and away from the user. Cylindrical body 342 also includes a depth marker 345 that indicates the implant impaction depth.

Figure 17:
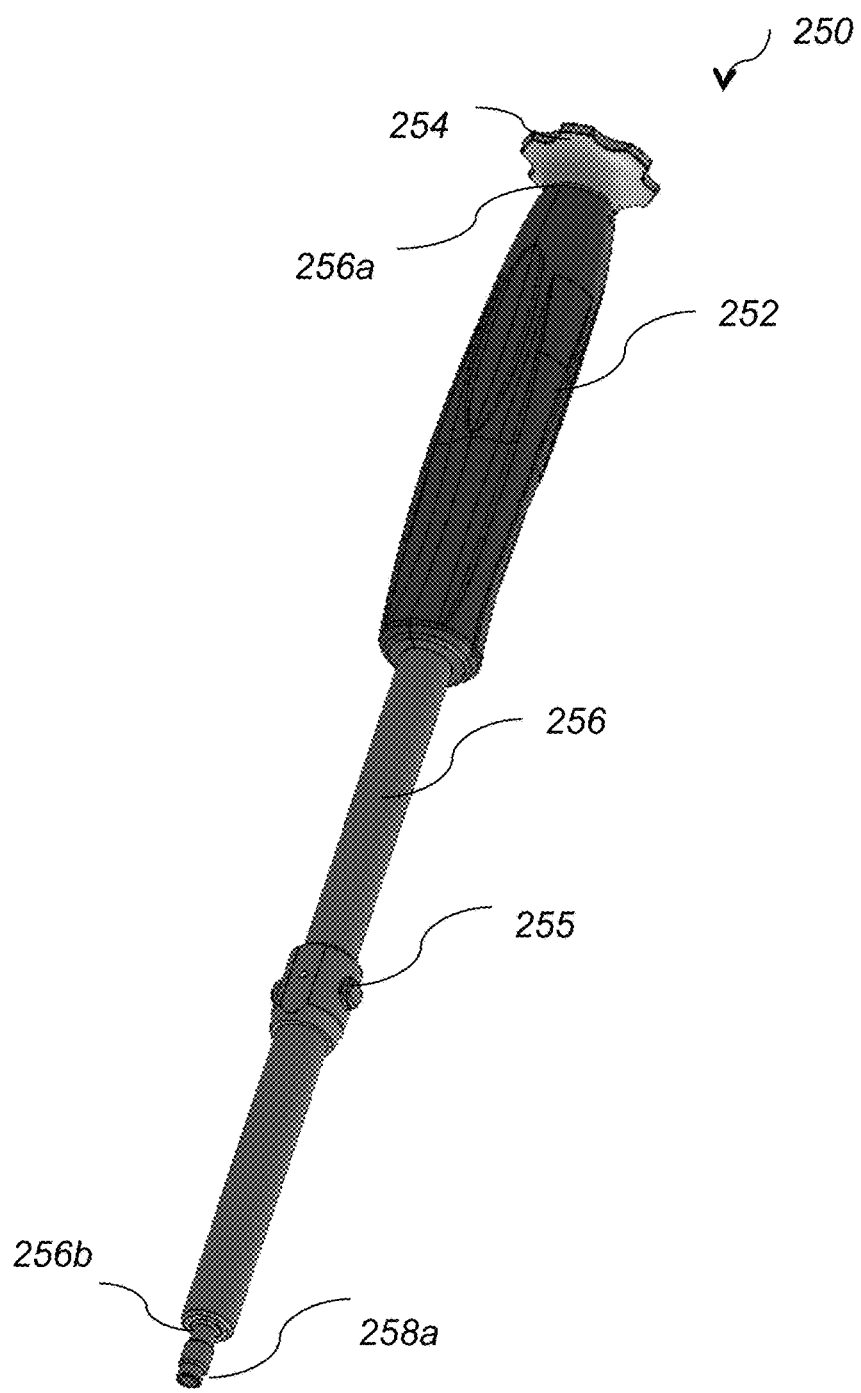
FIG. 17 is a perspective view of one example of an implant inserter tool, according to this invention.
Figure 18:
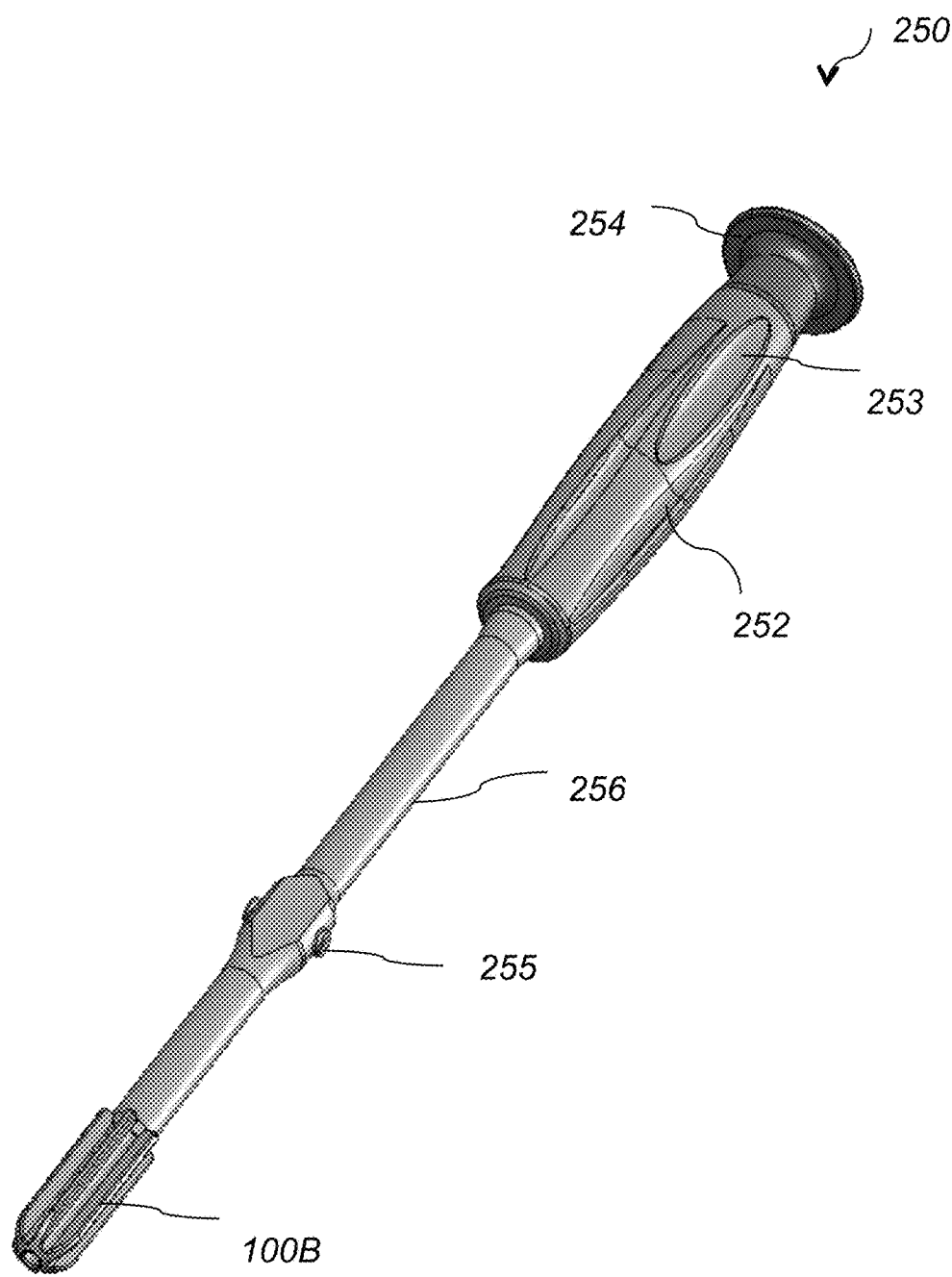
FIG. 18 is a perspective view of another example of an implant inserter tool with an attached implant, according to this invention.
Figure 19:
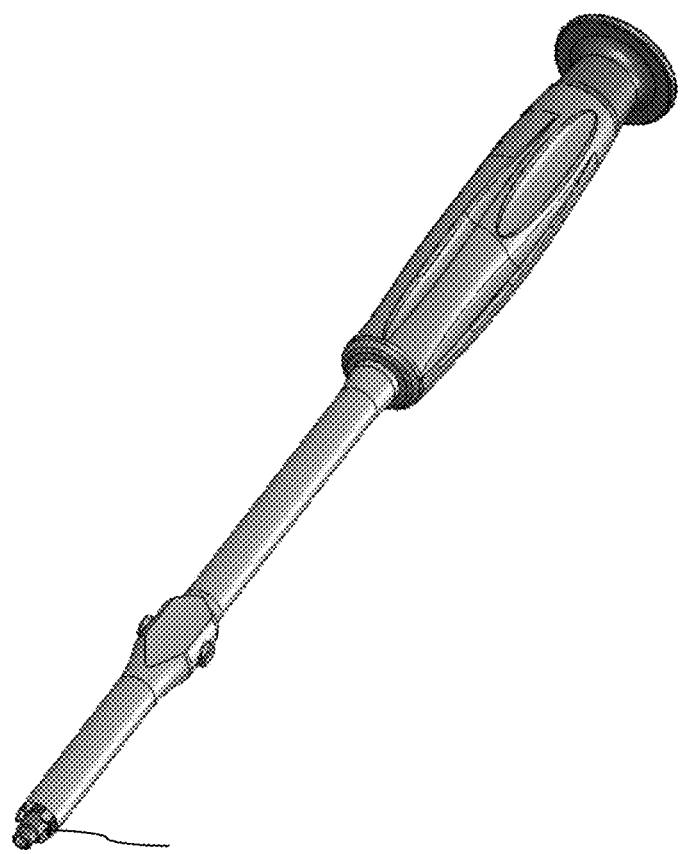
FIG. 19 is a perspective view of the implant inserter tool of FIG. 18 with a detached implant.
Figure 19:
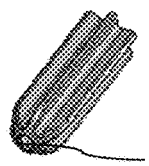

Referring to FIG. 17, FIG. 18 and FIG. 19, an implant inserter tool 250 includes an elongated cylindrical body 256 that includes an impaction area 254 at the proximal end 256a, a handle 252, alignment pins 255 and an implant holder 258a or 258b at the distal end 256b. Alignment pins 255 interface with the alignment channels 387 of the tissue protector 380. Implants 100A or 100B are removably attached to the implant holder 258a or 258b, respectively, which are shaped and dimensioned to interface with the back structure of the implants. As shown in FIG. 17, implant holder 258a has a threaded tip that engages inner threads within top opening 122 of implant 100A. Similarly, the threaded tip of implant holder 258b engages inner threads within top opening 162 of implant 100B. Implant holder 258b also includes implant anti-rotation features that interface with the star-shaped structure in the top of the implant 100B, as shown in FIG. 19.

In operation, pin guide 210 is used to insert pins 202a, 202b into two desired locations and form openings 92a, 92b through the ilium and the adjacent sacrum, respectively. The relative position and orientation of pins 202a, 202b is set by the pin guide 210. Next, a dilator 360 is inserted over the first or second pin 202a or 202b to dilate the tissue around the pins. Next, a tissue protector 380 is inserted over the dilator 360 and the dilator is removed leaving the pin 202a or 202b in place to form an opening to the ilium. Next, a cannulated drill is passed through the tissue protector over each of the pins and drilled into the ilium to a desired depth. Next, for implant 101a, a tap is used to tap threads in the formed opening 92a prior to inserting implant 101a. For implant 101b, a broach 300 is impacted into the bone to generate the opening pattern of implant 101b. Next, the bone fusing implants 101a, 101b are inserted into the corresponding formed openings 92a, 92b and the pin guides are removed. The steps are repeated for inserting pins for another implant.

Several embodiments of the present invention have been described. Nevertheless, it will be understood that various modifications may be made without departing from the spirit and scope of the invention. Accordingly, other embodiments are within the scope of the following claims.

What is claimed is:

1. A method for fusing two adjacent stacked bones comprising:
   inserting first and second pins into first and second locations of a first surface of one of the two adjacent stacked bones, respectively;
   inserting a dilator over each of the first and second pins to dilate tissue around the first and second pins;
   inserting a tissue protector over the dilator and removing the dilator;
   inserting a cannulated drill through the tissue protector over each of the first and second pins and drilling first and second openings in the first and second locations, respectively, wherein the first and second opening extend through the two adjacent stacked bones;
   tapping threads in the first opening and inserting a first bone fusing implant in the first opening, wherein the first bone fusing implant comprises threads configured to engage the threads of the first opening;
   impacting a broach into the second opening to generate a pattern corresponding to a pattern of a second bone fusing implant and then inserting the second bone fusing implant in the second opening; and
   removing the first and second pins from the first and second opening, respectively.

2. The method of claim 1, wherein one of the two adjacent stacked bones comprises a cortical bone and the other of the two adjacent stacked bones comprises a cancellous bone and wherein the first bone fusing implant comprises a first segment comprising cortical threads configured to engage threads in the cortical bone and a second segment comprising cancellous threads configured to engage threads in the cancellous bone.

3. The method of claim 2, wherein the cortical threads are closely spaced and have larger core-to-outer diameter ratio than the cancellous threads.

4. The method of claim 2, wherein the cancellous threads are cut deep and are widely spaced.

5. The method of claim 2 wherein the first segment comprises a length equal to the cortical bone width and wherein the second segment comprises a length equal to the cancellous bone width.

6. The method of claim 2, wherein the first bone fusing implant comprises a cylindrical hollow threaded body having a plurality of oval shaped openings and a central through-opening extending the entire length of the cylindrical hollow threaded body.

7. The method of claim 2, wherein the first bone fusing implant comprises one of bone, polyetheretherketone (PEEK), Nitinol, metals, titanium, steel, metal composites, biodegradable materials, collagen matrices, synthetic polymers, polysaccharides, calcium minerals, calcium salts, or composites containing calcium or phosphorous naturally or man made.

8. The method of claim 1, wherein the second bone fusing implant comprises a star-shaped hollow elongated body that has a central through-opening and outer ridges that are configured to engage grooves formed in an inner surface of the second opening.

9. The method of claim 8, wherein an outer surface of the second bone fusing implant is coated with bone growth enhancing additives and wherein the bone growth enhancing additives comprise one of calcium phosphates, or hydroxyapatite.

10. The method of claim 1, wherein the first and second pins are inserted into the first and second locations of the first surface of one of the two adjacent stacked bones via a pin guide tool and wherein the pin guide tool is configured to set relative position, distance, pin depth and pin orientation of the first and second pins.

11. The method of claim 10, wherein the pin guide tool comprises a main body, and a pin alignment slide and wherein the main body comprises an upper portion and a lower portion and wherein the upper portion extends along a first direction perpendicular to the lower portion and comprises a cylindrical through-opening shaped and dimensioned to slidably receive the first pin, and wherein the pin alignment slide comprises a cylindrical through-opening extending parallel to the cylindrical through-opening of the upper portion and being shaped and dimensioned to slidably receive the second pin.

12. The method of claim 11, wherein the upper portion of the main body comprises markings indicating the diameter of the first bone fusing implant and wherein the pin alignment slide comprises markings indicating the diameter of the second bone fusing implant.

13. The method of claim 11, wherein the pin alignment slide comprises a through-slot shaped and dimensioned to slidably receive the lower portion of the main body and wherein the pin alignment slide is configured to set the distance between the first and second pins by sliding along the lower portion of the main body in a direction perpendicular to the first direction.

14. The method of claim 13, wherein the lower portion of the main body comprises a slide with teeth and wherein the pin alignment slide is configured to slide along the slide and the position of the pin alignment slide is secured along the slide by engaging a lever.

15. The method of claim 1, wherein the dilator comprises a cylindrical body with a central through-opening shaped and dimensioned to slide over the first and second pins, and wherein the cylindrical body of the dilator comprises a segment with recessed parallel surfaces, curved upper and lower edges and a depth marker.

16. The method of claim 1, wherein the tissue protector comprises a tubular hollow cylindrical body having a proximal end and an angled distal end and wherein the angled distal end comprises teeth and wherein the proximal end comprises a ring-shaped surface surrounding a lumen and wherein the lumen comprises first and second opposite alignment channels.

17. The method of claim 16, wherein the tissue protector further comprises an elongated detachable handle and a table mount ring extending from an edge of the ring-shaped surface and wherein the elongated detachable handle is configured to be attached to locations around the ring-shaped surface.

18. The method of claim 1, wherein the broach comprises an elongated cylindrical body having an impaction area at a proximal end and alignment pins at a distal end and wherein the broach further comprises a tissue tapping end effector configured to be removably attached to the distal end.

19. The method of claim 18, wherein the impaction area comprises a flat top surface and a side notch.

20. The method of claim 18, wherein the tissue tapping end effector comprises outer cutting surfaces configured to generate the pattern of the second bone fusing implant in the second opening.

21. The method of claim 19, wherein the elongated cylindrical body comprises a curved channel formed along a side surface of the elongated cylindrical body and being configured to receive a guide wire and wherein the curved channel is aligned with the side notch of the impaction area.

22. The method of claim 21, wherein the tissue tapping end effector comprises a through-opening configured to receive the guide wire.

23. The method of claim 18, wherein the cylindrical body further comprises depth markers configured to indicate a tapping depth.

24. The method of claim 1, wherein the first and second bone fusing implants are inserted with an implant inserter tool and wherein the implant inserter tool comprises an elongated cylindrical body, a handle, an impaction area, alignment pins and an implant holder and wherein the impaction area is located at a proximal end of the elongated cylindrical body and the implant holder is attached to a distal end of the elongated cylindrical body and wherein the implant holder comprises structures configured to engage corresponding structures on a proximal end of the first and second bone implants.

* * * * *